United States Patent
Hanes et al.

(10) Patent No.: US 11,228,829 B2
(45) Date of Patent: Jan. 18, 2022

(54) REGULATING ENVIRONMENTAL CONDITIONS INSIDE CUPS OF HEADPHONES

(71) Applicant: HEWLETT-PACKARD DEVELOPMENT COMPANY, L.P., Houston, TX (US)

(72) Inventors: David H. Hanes, Fort Collins, CO (US); Jon R. Dory, Fort Collins, CO (US); John Michael Main, Fort Collins, CO (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 750 days.

(21) Appl. No.: 16/076,909

(22) PCT Filed: Jul. 14, 2017

(86) PCT No.: PCT/US2017/042167
§ 371 (c)(1),
(2) Date: Aug. 9, 2018

(87) PCT Pub. No.: WO2019/013823
PCT Pub. Date: Jan. 17, 2019

(65) Prior Publication Data
US 2021/0204051 A1    Jul. 1, 2021

(51) Int. Cl.
*H04R 1/10*    (2006.01)

(52) U.S. Cl.
CPC ......... *H04R 1/1041* (2013.01); *H04R 1/1008* (2013.01); *H04R 1/1075* (2013.01); *H04R 1/1091* (2013.01); *H04R 2460/11* (2013.01)

(58) Field of Classification Search
CPC .. H04R 1/1041; H04R 1/1008; H04R 1/1075; H04R 1/1091
See application file for complete search history.

(56) References Cited

U.S. PATENT DOCUMENTS

| 5,864,989 A | 2/1999 | Funatsu et al. |
| 9,208,769 B2 | 12/2015 | Azmi |
| (Continued) | | |

FOREIGN PATENT DOCUMENTS

| CN | 201156817 Y | 11/2008 |
| CN | 101494811 A | 7/2009 |
| (Continued) | | |

OTHER PUBLICATIONS

Miletic, "Air-Cooled Gamers Headsets", Cyber Shack, Retrieved from Internet—http://www.cybershack.com.au/news/air-cooled-gamers-headsets, 2007, 4 Pages.

(Continued)

*Primary Examiner* — Simon King
(74) *Attorney, Agent, or Firm* — Fabian VanCott (57) ABSTRACT

Headphones include a pair of cups, each housing a speaker to be positioned over an ear of a user, a processor, a cooling mechanism disposed within each of the cups to regulate environmental conditions inside of the cups to match environmental thresholds provided by a virtual reality device displaying a virtual reality environment to the user, a temperature sensor and at least one additional environmental sensor disposed within each of the cups to monitor the environmental conditions inside the cups, the processor to subsequently analyze data associated with the sensors and compare the data to the environmental thresholds and the processor to selectively activate the cooling mechanism based on the comparison.

20 Claims, 11 Drawing Sheets

(56) References Cited

U.S. PATENT DOCUMENTS

| | | | |
|---|---|---|---|
| 9,270,244 B2 | 2/2016 | Usher et al. | |
| 9,664,902 B1 | 5/2017 | Raffle et al. | |
| 9,942,647 B2 | 4/2018 | Di Censo | |
| 2001/0045919 A1 | 11/2001 | Ishikawa et al. | |
| 2001/0046304 A1 | 11/2001 | Rast | |
| 2003/0215108 A1 | 11/2003 | Shelley et al. | |
| 2005/0105755 A1 | 5/2005 | Yueh et al. | |
| 2006/0017654 A1 | 1/2006 | Romo | |
| 2010/0095439 A1 | 4/2010 | Nolan et al. | |
| 2011/0268290 A1 | 11/2011 | Lee | |
| 2012/0207320 A1 | 8/2012 | Avital | |
| 2014/0079257 A1 | 3/2014 | Ruwe et al. | |
| 2014/0169751 A1* | 6/2014 | Weast | H04N 21/4436 386/200 |
| 2015/0281829 A1 | 10/2015 | Gauger, Jr. | |
| 2015/0302651 A1 | 10/2015 | Shpigelman | |
| 2016/0192050 A1 | 6/2016 | Masaki et al. | |
| 2016/0243701 A1* | 8/2016 | Gildert | G05B 19/42 |
| 2016/0323664 A1 | 11/2016 | Kirsch | |
| 2016/0381415 A1 | 12/2016 | Vijay et al. | |
| 2017/0049335 A1 | 2/2017 | Duddy | |
| 2017/0099539 A1* | 4/2017 | Di Censo | H04R 1/1008 |
| 2017/0109131 A1* | 4/2017 | Boesen | G06F 3/012 |
| 2018/0286080 A1* | 10/2018 | Marshall | G02B 27/017 |

FOREIGN PATENT DOCUMENTS

| | | |
|---|---|---|
| CN | 101513083 B | 9/2011 |
| CN | 202261733 | 5/2012 |
| CN | 102647640 A | 8/2012 |
| CN | 205408108 U | 7/2016 |
| CN | 106851448 A | 6/2017 |
| CN | 106445176 B | 10/2018 |
| EP | 2851001 | 11/2016 |
| EP | 3089474 | 11/2016 |
| WO | 2015163913 A1 | 10/2015 |
| WO | 2015192117 A1 | 12/2015 |
| WO | WO-2016148316 | 9/2016 |
| WO | 2016161450 A1 | 10/2016 |

OTHER PUBLICATIONS

O'Kane, S., Smart Headphones with Voice Recognition Could Help You Miss Fewer Conversations, Dec. 5, 2016 <https://www.theverge.com/circuitbreaker/2016/12/5/1384-1776/stages-hero-headphones-noise-cancellation-augemented-sound>.

* cited by examiner

| Table 800 | | |
|---|---|---|
| Environmental Condition(s) 820 | Environmental Threshold(s) 842 | Activate Cooling Mechanism(s) 844 |
| Environmental Condition A 820-1 | Environmental Threshold A 842-1 | Both Cooling Mechanisms 844-1 |
| Environmental Condition B 820-2 | Environmental Threshold B 842-2 | No 844-2 |
| Environmental Condition C 820-3 | Environmental Threshold C 842-3 | Left Cooling Mechanism 844-3 |
| Environmental Condition D 820-4 | Environmental Threshold D 842-4 | Right Cooling Mechanism 844-4 |

REGULATING ENVIRONMENTAL CONDITIONS INSIDE CUPS OF HEADPHONES

BACKGROUND

Many devices can be used to display audiovisual media including a smart phone, a tablet, an MP3 player, or a computer. A virtual reality (VR) system, however, seeks to more completely immerse the user in audiovisual media. To immerse the user in audiovisual media, a VR system includes a display and connects to other devices such as headphones. The display presents the visual component of the audiovisual media. The headphones present the audio. Headphones are designed to be worn on or around the head of the user and may fit over the user's ears. With headphones over the user's ears, ambient sound may be less perceptible to enhance the feeling of immersion in the VR media

BRIEF DESCRIPTION OF THE DRAWINGS

The accompanying drawings illustrate various examples of the principles described herein and are a part of the specification. The examples do not limit the scope of the claims.

Throughout the drawings, identical reference numbers designate similar, but not necessarily identical, elements.

DETAILED DESCRIPTION

As noted above, to immerse the user in audiovisual media, a device includes a display and connects to another device such as headphones. These headphones are often designed to minimize or block out ambient sounds. For example, some headphones have large cups that surround the outer ear of the user. This allows the headphones to fully seal against the users head around the ears to attenuate perception of ambient sounds.

However, during long periods of use, environmental conditions such as temperature and humidity inside of the cups tends to increase. This may cause the headphones to become uncomfortable to wear. As a result, the user physically removes the headphones to allow cooler air external to the cups of the headphones to circulate thus reducing the temperature and humidity inside of the cups. Once the temperature and humidity inside of the cups is reduced to the user's satisfaction, the user may replace the headphones. The manual removal and replacement of the headphones can be an annoyance and may interrupt the users immersion in the audiovisual media.

In one example described herein, a set of headphones includes: a pair of cups, each housing a speaker to be positioned over an ear of a user; a processor; a cooling mechanism disposed within each of the cups to regulate environmental conditions inside of the cups to match environmental thresholds provided by a virtual reality device displaying a virtual reality environment to the user; and a temperature sensor and at least one additional environmental sensor disposed within each of the cups to monitor the environmental conditions inside the cups; the processor to subsequently analyze data associated with the sensors and compare the data to the environmental thresholds; and the processor to, in response to the data for all of the sensors indicating all of the environmental conditions exceed all the environmental thresholds, activate the cooling mechanism such that the cooling mechanism regulates the environmental conditions inside of cups of headphones until the data for each of the sensors indicates the environmental conditions match the environmental thresholds.

In another example, a system includes: a virtual reality device comprising an output to a virtual reality (VR) headset with headphones, the virtual reality device to provide the headset with environmental thresholds associated with a virtual reality environment being displayed to the user via the virtual reality device. The VR headset with headphones includes: a pair of cups, each housing a speaker to be positioned over an ear of a user; a processor; a cooling mechanism disposed within each of the cups to regulate environmental conditions inside of the cups to match the environmental thresholds; and a temperature sensor and at least one additional environmental sensor disposed within each of the cups to monitor the environmental conditions inside the cups; the processor to subsequently analyze data associated with the sensors and compare the data to the environmental thresholds; and the processor to, in response to all of the sensors indicating all of the environmental conditions exceed the environmental thresholds, activate the cooling mechanism such that the cooling mechanism regulates the environmental conditions inside of cups of headphones until the data for each of the sensors indicates the environmental conditions do not exceed the environmental thresholds.

In another example, a method includes: receiving, via a virtual reality device, a number of thresholds associated with a virtual reality environment being displayed to a user; with a temperature sensor and at least one additional environmental sensor disposed within each of cups of headphones monitoring environmental conditions inside the cups; and activating, via a processor, the cooling mechanism in response to all of the sensors indicating all of the environmental conditions exceed the environmental thresholds such that the cooling mechanism regulates the environmental conditions inside of cups of headphones until the data for each of the sensors indicates the environmental conditions do not exceed the environmental thresholds.

Figure 1A:
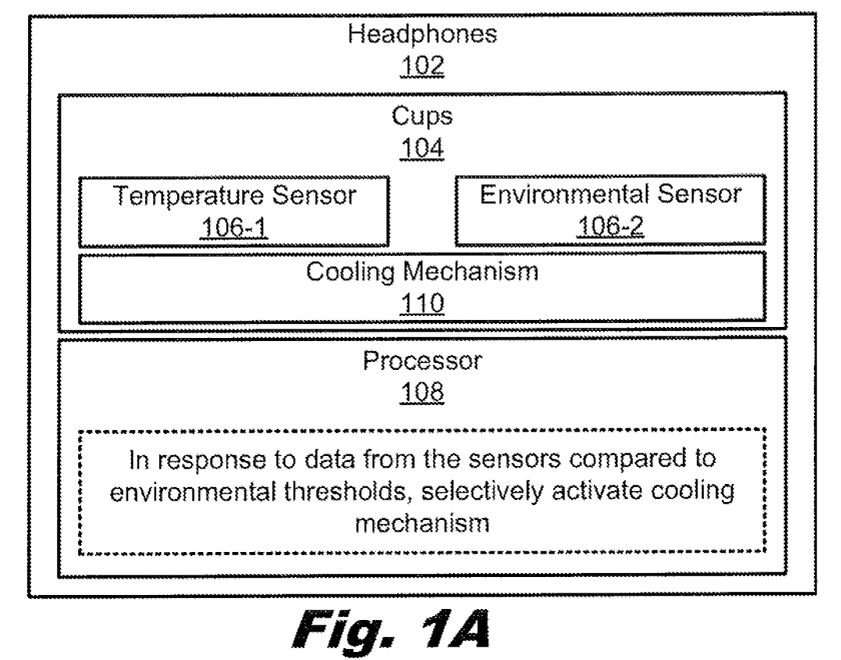
FIG. 1A is a diagram of headphones for regulating environmental conditions inside cups of the headphones, according to one example of principles described herein.

Referring now to the figures, FIG. 1A is a diagram of an example of headphones including a system for regulating environmental conditions inside the cups of the headphones. As illustrated, the set of headphones (102) includes a pair of cups (104), each housing a speaker to be positioned over an ear of a user. A cooling mechanism (110) is disposed within each of the cups (104) to regulate environmental conditions inside of the cups (104).

The headphones (102) also include a number of sensors (106) to detect environmental conditions inside the cups (104). In the illustrated example, a temperature sensor (106-1) and at least one additional environmental sensor (106-2) are disposed within each of the cups (104) to monitor the environmental conditions inside the cups (104).

A processor (108) subsequently analyzes data output by the sensors (106) and compares the data to environmental thresholds. In some examples, environmental thresholds may be set by the user. In other examples, the environmental thresholds may be provided by a virtual reality device presenting a virtual reality environment to the user so that the environmental conditions inside the cups correspond to the virtual reality environment being presented. For example, the environmental thresholds could be provided by or derived from the file being used to generate and present the VR environment. Additionally, the processor (108) may access a file that tags one or more specified scenes in the VR with corresponding environmental thresholds. Consequently, when a specified scene is being presented by the VR system, the corresponding environmental thresholds from the file are used by the processor (108) as described herein. Additionally, users may create such files with specified environmental thresholds for identified scenes in the VR. Such filed might be uploaded to the Internet or other network to be shared for downloading and use by other users.

In response to the environmental conditions detected by the sensors (106) exceeding, in some way, the environmental thresholds, the processor (106) operates the cooling mechanism (110) to change the environmental conditions in the cups (104). Different combinations of sensed environmental parameters compared to established thresholds may evoke different responses from, the processor (108). For example, the processor (108) may not activate the cooling mechanism (110) until all of multiple sensed environmental parameters in the cups (104) exceed corresponding and respective thresholds. Alternatively, the processor (108) may activate the cooling mechanism (110) if any of multiple sensed environmental parameters in the cups (104) exceeds a corresponding threshold.

In other examples, one of the environmental parameters may be designated as dominant. For example, the temperature may be considered the dominant environmental parameter. In such a case, if the user's heartrate is too high, the system may activate cooling. However, if the temperature then drops to or below a lower threshold, even without the user's heartrate coming down, the system may deactivate the cooling because temperature is the dominant environmental parameter. Any set of conditions relating the different environmental parameters and when to activate or deactivate cooling would be within examples of the system being described. For example, a two or three-dimensional table relating the different environmental parameters and the system's response to activate or deactivate cooling could be provided as a lookup for the processor (108).

Once activated, the cooling mechanism (110) regulates the environmental conditions inside of cups (104) of headphones (102) until the data from the sensors (106) indicates the environmental condition or conditions that triggered activation of the cooling mechanism (110) no longer exceed(s) the established environmental thresholds.

Figure 1B:
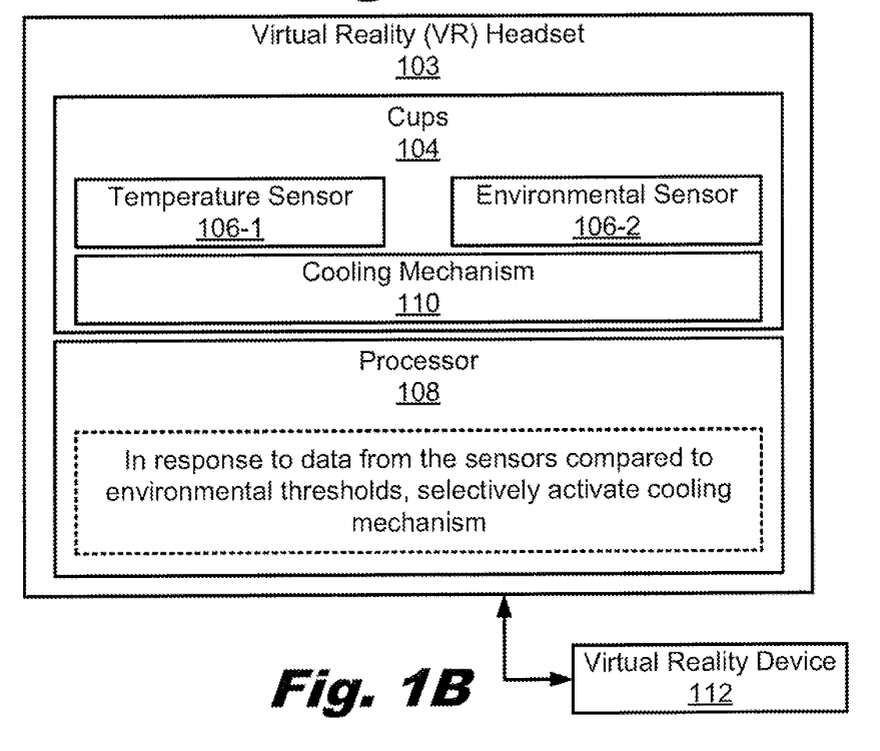
FIG. 1B is a diagram of a system for regulating environmental conditions inside cups of headphones, according to one example of principles described herein.

FIG. 1B is a diagram of a system for regulating environmental conditions inside cups of the headphones, according to one example of principles described herein. As will be described below, this system is similar to that illustrated in FIG. 1A and described above, except that this system includes a virtual reality device (112) and the headphones are incorporated in a virtual reality headset (103).

Figure 2:
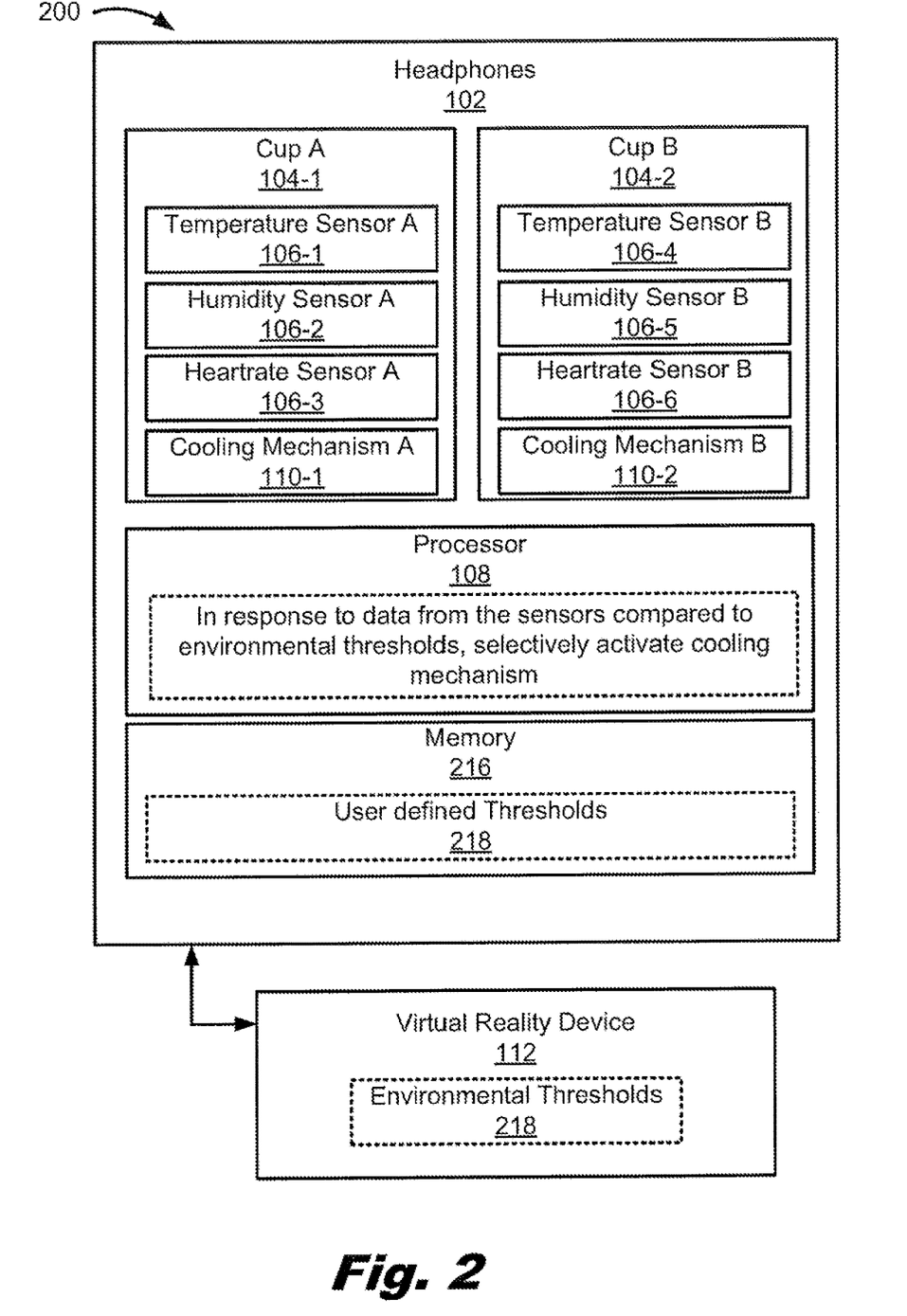
FIG. 2 is a diagram of a system for regulating environmental conditions inside cups of headphones, according to one example of principles described herein.

The virtual reality device (112) in communication with the virtual reality headset (103) with headphones (102) provides the headset (103) with environmental thresholds associated with a virtual reality. Consequently, the environmental thresholds applied by the processor (108) come from the virtual reality device and may coordinate the environmental conditions in the cups (104) with the virtual reality environment being presented. For example, if the virtual reality environment being presented is perceived as a relatively hot environment, a temperature threshold output by the virtual reality device (112) may be elevated. Similarly, if the virtual reality environment is a cold environment, a temperature threshold output by the virtual reality device (112) may be relative lower, perhaps lower than room temperature, FIG. 2 is a diagram of system for regulating environmental conditions inside cups of headphones, according to one example of principles described herein. As will be described below, system (200) includes a virtual reality device (112) and headphones (102).

As illustrated, the system (200) includes a virtual reality device (112) in communication with headphones (102) to provide the headphones (102) with environmental thresholds (218) associated with a virtual reality environment being displayed to the user via the virtual reality device (112). In an example, the environmental thresholds (218) include a temperature threshold associated with a virtual reality environment being displayed to the user. For example, if the associated a virtual reality environment being displayed to the user is a beach, that temperature threshold may be 80 degrees. However, if the associated a virtual reality environment being displayed to the user is a snowstorm, that temperature threshold may be 32 degrees.

In an example, the environmental thresholds (218) include a humidity threshold associated with a virtual reality environment being displayed to the user. For example, if the associated a virtual reality environment being displayed to the user is a beach, that humidity threshold may be 76 percent humidity. However, if the associated a virtual reality environment being displayed to the user is a rainstorm, that humidity threshold may be 100 percent humidity.

In some examples, the environmental thresholds (218) are determined by a user when the headphones (102) are not in communication with the virtual reality device (112). For example, a user input button allows the user to set a temperature threshold, a humidity level threshold and a heartrate threshold. More information about the environmental thresholds (218) will be described below.

As illustrated in FIG. 2, the headphones (102) include a pair of cups (104). For example, the headphones (102) include cup A (104-1) and cup B (104-2). The cups (104) include large pads that surround the outer ear of the user allowing the cups (104) of the headphones (102) to fully seal against the ears of the user. For example, cup A (104-1) surrounds the left ear of the user and cup B (104-2) surrounds the right ear of the user.

Each of the cups (104) house a speaker to be positioned over an ear of a user. For example, cup A (104-1) includes speaker A and cup B (104-2) includes speaker B. The speakers are acoustical transducers that allow information to be presented to the user in an audio form.

The headphones (102) include a number of sensors (106) disposed within each of the cups (104) to monitor the environmental conditions inside the cups (104). For example, temperature sensor A (106-1) is disposed within cup A (104-1) to monitor the temperature inside the cup A (104-1). Similarly, temperature sensor B (106-4) is disposed within cup B (104-2) to monitor the temperature inside the cup B (104-2).

As mentioned above, a cooling mechanism (110) is disposed within each of the cups (104) to regulate environmental conditions inside of the cups (104) to match established environmental thresholds. As illustrated, cup A (104-1) includes cooling mechanism A (110-1) and cup B (104-2) includes cooling mechanism B (110-2). These cooling mechanisms (110) are controlled by the processor (108).

In one example, the temperature sensors (106-1 and 106-4) monitor a temperature level inside of the cups (104) of the headphones (102) such that when the temperature inside of the cups (104) of headphones (102) exceeds a temperature threshold as indicated by one of the environmental thresholds (218), the cooling mechanisms (110) are activated to regulate the temperature inside of the cups (104) of the headphones (102) until the temperature inside of the cups (104) matches that temperature threshold. For example, if the temperature threshold for both cups (104) is 75 degrees and the temperature sensor A (106-1) and temperature sensor B (106-4) indicate the temperature inside of the cups are 80 degrees, the cooling mechanisms (110) are activated to regulate the temperature inside of the cups (104) of the headphones (102) until the temperature inside of the cups (104) matches 75 degrees.

Humidity sensor A (106-2) is disposed within cup A (104-1) to monitor the humidity inside the cup A (104-1). Similarly, humidity sensor B (106-5) is disposed within cup B (104-2) to monitor the humidity inside the cup B (104-2). In an example, the humidity sensors (106-2 and 106-5) monitor a humidity level inside of the cups (104) of the headphones (102) such that when the humidity level inside of the cups (104) of headphones (102) exceeds a humidity threshold as indicated by one of the environmental thresholds (218), the cooling mechanisms (110) are activated to regulate the humidity level inside of the cups (104) of the headphones (102) until the humidity level inside of the cups (104) matches that humidity threshold.

For example, if the humidity threshold for both cups (104) is 50 percent and the Humidity sensor A (106-2) and humidity sensor B (106-5) indicate the humidity level inside of the cups are 55 percent, the cooling mechanisms (110) are activated to regulate the humidity level inside of the cups (104) of the headphones (102) until the humidity level inside of the cups (104) matches 50 percent.

Heartrate sensor A (106-3) is disposed within cup A (104-1) to monitor the user's heartrate at cup A (104-1). Similarly, heartrate sensor B (106-6) is disposed within cup 13 (104-2) to monitor the user's heartrate at cup B (104-2). In an example, the heartrate sensors (106-3 and 106-6) monitoring a heartrate of the user wearing the headphones (102) such that when the users heartrate exceeds a heartrate threshold as indicated by one of the environmental thresholds, the cooling mechanisms (110) are activated to regulate the environmental conditions inside of the cups (104) of the headphones (102) to reduce the user's heartrate.

For example, if the heartrate threshold for the user is 100 beats per minute and the heartrate sensor A (106-3) and/or heartrate sensor B (106-6) indicates the user's heartrate is 120 beats per minute, the cooling mechanisms (110) are activated to regulate environmental conditions of the cups (104) until the users heartrate is below 100 beats per minute.

As will be described in subsequent figures, the cooling mechanism (110) in each of the cups (104) may be one of a number of different cooling mechanism. One example includes a motor rotatable coupled to a fan. In another example, the cooling mechanism (110) in each of the cups (104) includes a refrigeration device based on a Peltier effect, for example, a semiconductor chip. In yet another example, the cooling mechanism (110) in each of the cups (104) includes an acoustic transducer. In another example, the cooling mechanism (110) in each of the cups (104) includes a member and an actuator, the member is pivotally connected to the cup via a hinge. In another example, the cooling mechanism (110) in each of the cups (104) includes a member and an actuator, wherein the member is rotatably connected to the cup.

FIGS. 3A to 4B will describe a number of embodiments of the headphones (102) with different types of cooling mechanisms (110). While FIGS. 3A to 4B illustrate a portion of the headphones (102), it should be understood that the principles apply to both cups (104) and components thereof.

Figure 3A:
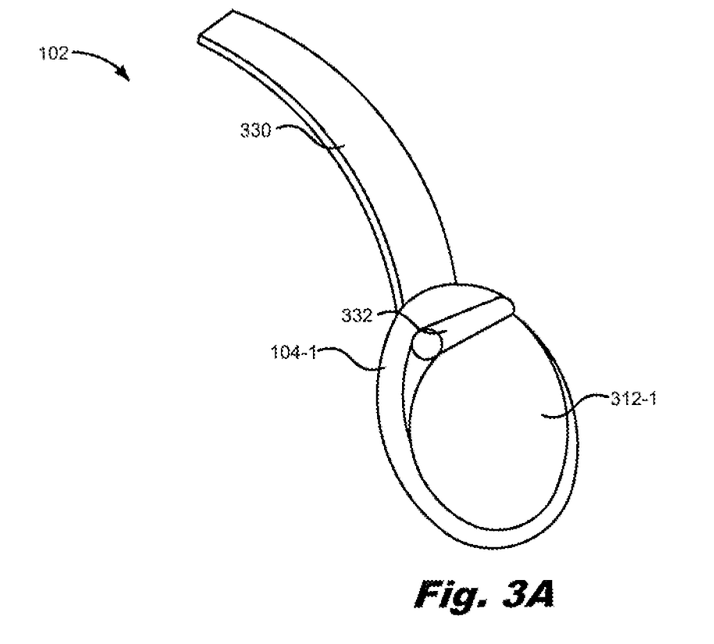
FIG. 3A is a diagram of a set of headphones with a member of the headphones in a closed position, according to one example of principles described herein.

Turning specifically to FIG. 3A, FIG. 3A is a diagram of a set of headphones with a member of the headphones in a closed position, according to one example of principles described herein. As will be described below, the member (312-1) is pivotally connected to the cup (104-1) via a hinge (332).

As illustrated in FIG. 3A, the headphones (102) include a band (330). In some examples, the band (330) is placed over a top portion of the users head such that the cups (104) are positioned over the ears of the user. In other examples, the band may run behind the user's head between the ears or have some other configuration.

The headphones include the cup (104-1). The portion of the cup (104-1) is connected to a portion of the band (330) as illustrated in FIG. 3A. Again, although only one cup (104-1) is illustrated in FIG. 3A, the headphones (102) include an additional cup as described above.

The cup (104-1) of the headphones is pivotally connected to the member (312-1) via the hinge (332). As illustrated in FIG. 3A, the member (312-1) is in a closed position.

Figure 3B:
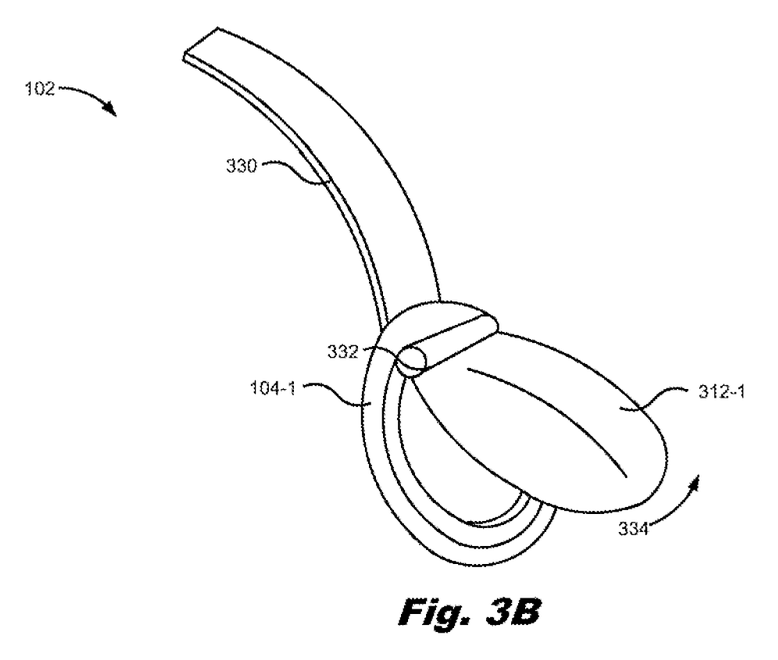
FIG. 3B is a diagram of a set of headphones with a member of the headphones in an open position, according to one example of principles described herein.

FIG. 3B is a diagram of a set of headphones with a member of the headphones in an open position, according to one example of principles described herein. As mentioned above, the member (312-1) is pivotally connected to the cup (104-1) via a hinge (332).

In an example, when the processor (108) selectively activates the cooling mechanisms (110), the actuator (not illustrated) pivots the member (312-1) as indicated by arrow 334 to open an aperture through the cup (104) such that air located inside of the cup (104-1) of the headphones (102) is exchanged with air located external to the cups (104-1) until the data for each of the sensors (106) indicates the environmental conditions match the environmental thresholds.

Figure 4A:
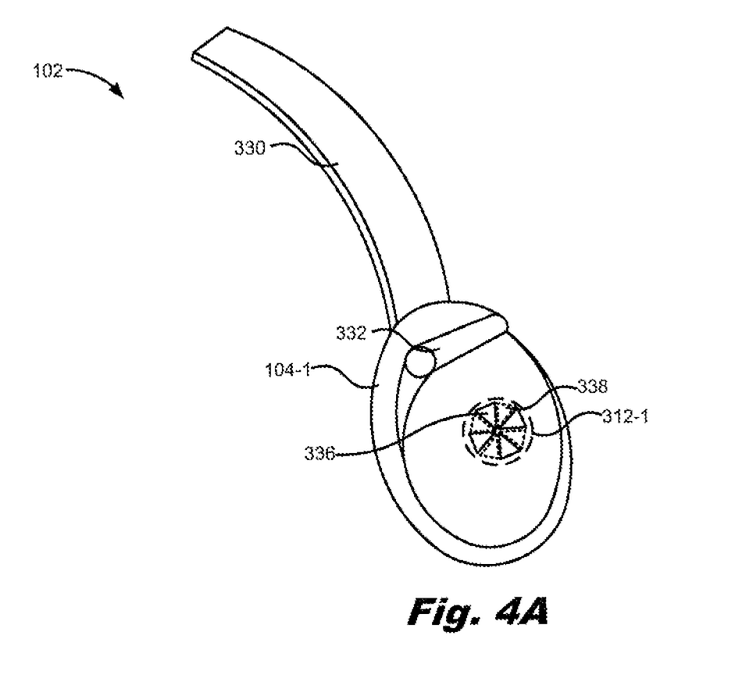
FIG. 4A is a diagram of a set of headphones with a member of the headphones in a closed position, according to one example of principles described herein.

While the examples and drawings of FIGS. 3A and 3B illustrate one of the members (312-1) of the cups (104)

pivoting, the other members of the other cups (104) may pivot as well. As a result, one or both of the members (312) for the cups (104) can pivot FIG. 4A is a diagram of a set of headphones with a member of the headphones in a closed position, according to one example of principles described herein. As will be described below, the member (312-1) is rotatably connected to the cup (104-1).

In this example, the cup (104-1) includes a number of cup apertures (336). Further, the member (312-1) includes a number of member apertures (338). As illustrated in FIG. 4A, the member (312-1) is rotated such that cup apertures (336) do not line up with the member apertures (338). As a result, the environmental conditional cannot be regulated. As will be described in FIG. 4B, when the processor (108) selectively activates the actuator (not shown), the member (312-1) rotates (340).

Figure 4B:
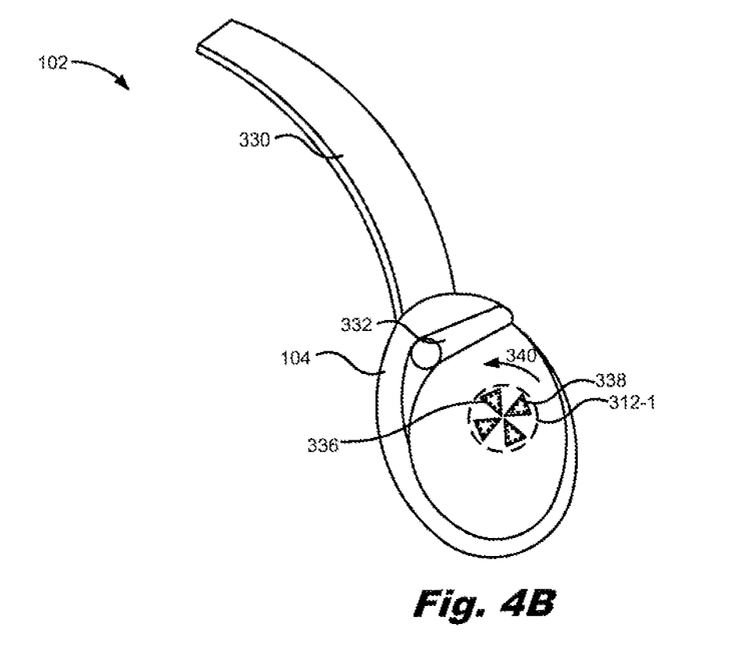
FIG. 4B is a diagram of a set of headphones with a member of the headphones in an open position, according to one example of principles described herein.

FIG. 46 is a diagram of a set of headphones with a member of the headphones in an open position, according to one example of principles described herein. As mentioned adobe, the cooling mechanisms (110) in each of the cups (104) includes a member (312) and a actuator, The member (312-1) is rotatably connected to the cup (104-1) such that, when the processor (108) selectively activates the cooling mechanisms (110), the actuator rotates the member (312-1) relative to the cup (104-1) such that cup apertures (336) line up with the member apertures (338) to open an aperture through the cup (104-1) such that that air located inside of the cup (104-1) of the headphones is exchanged with air located external to the cups (104) until the data for each of the sensors (106) indicates the environmental conditions match the environmental thresholds.

Figure 5:
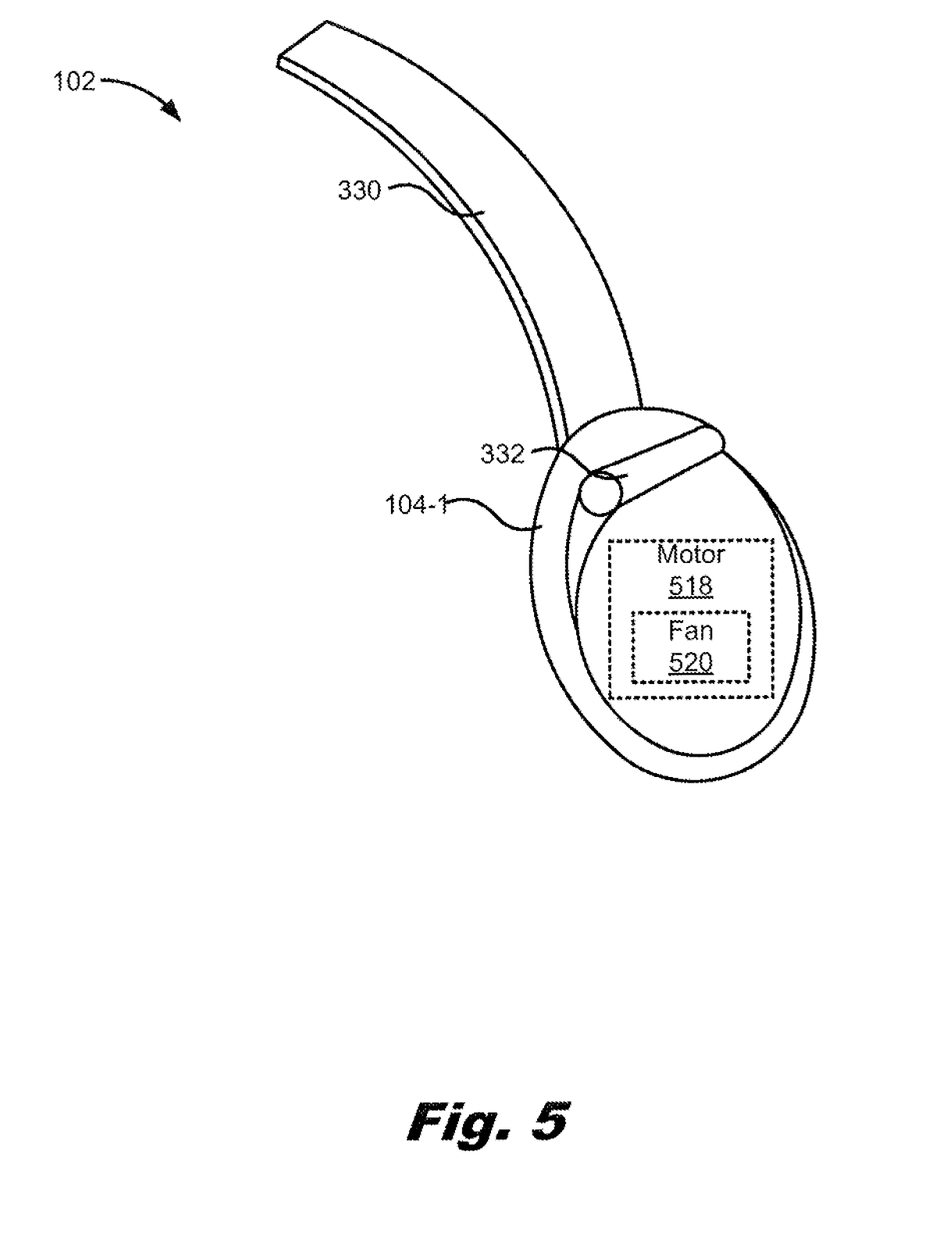
FIG. 5 is a diagram of a set of headphones with a fan coupled to a motor as a cooling mechanism, according to one example of principles described herein.

FIG. 5 is a diagram of a set of headphones with a fan coupled to a motor as a cooling mechanism, according to one example of principles described herein. As will be described below, the cooling mechanism (110) is a motor (518) rotatable coupled to a fan (520).

The cooling mechanism (110) in each of the cups (104) includes is a motor (518) rotatable coupled to a fan (520), the motor (518) rotating the fan (620) as instructed by the processor at a specified revolutions per minute (RPM) such that the fan (520) exchanges air located inside of the cups (104) of the headphones (102) with air located external to the cups (104) via an aperture in each of the cups (104) until the data for each of the sensors (106) indicates the environmental conditions match the environmental thresholds. In some examples, the RPM is between 10 to 30 RPM to reduce the noise generated by the fan (520) such that the noise does not interfere with the audio of the headphones (102).

Figure 6:
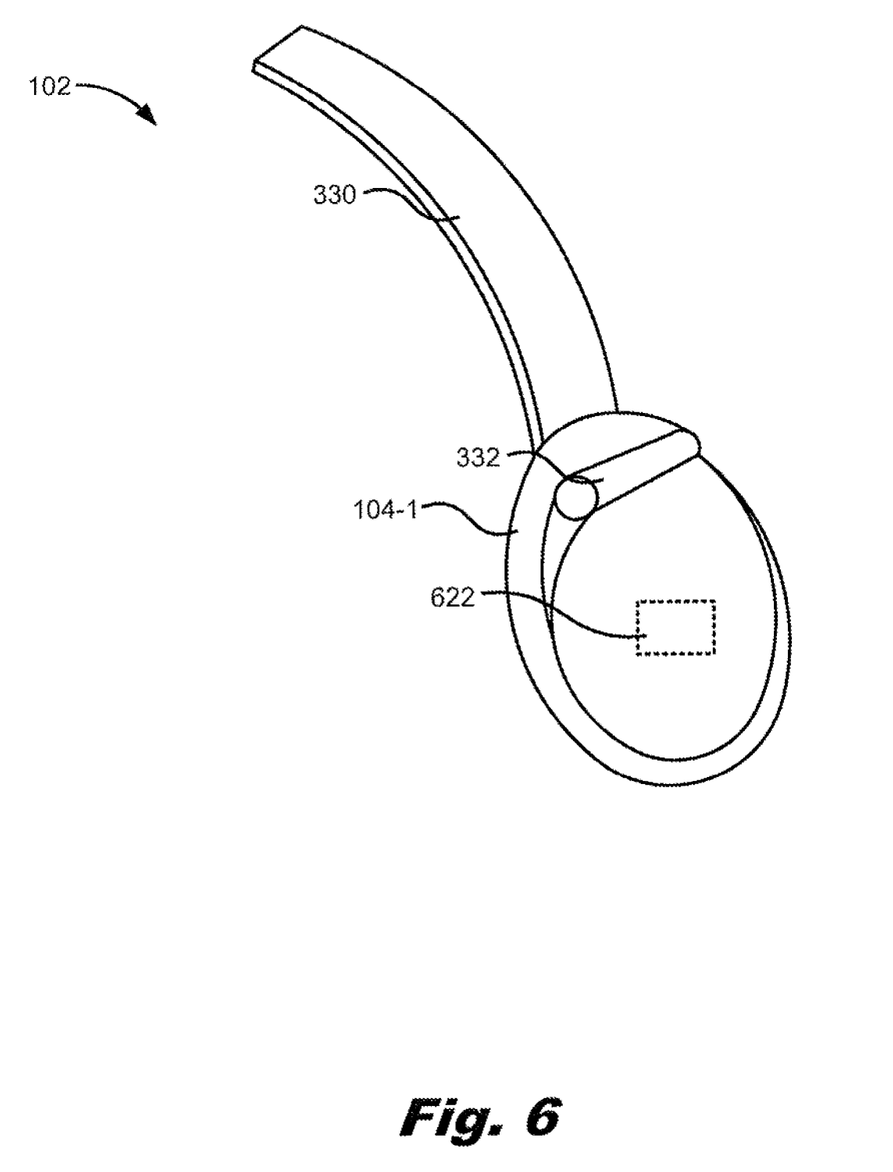
FIG. 6 is a diagram of a set of headphones with a semiconductor refrigeration chip as a cooling mechanism, according to one example of principles described herein.

FIG. 6 is a diagram of a set of headphones with a semiconductor refrigeration chip as a cooling mechanism, according to one example of principles described herein. As will be described below, the cooling mechanism (110) is a semiconductor refrigeration chip (622).

Figure 7:
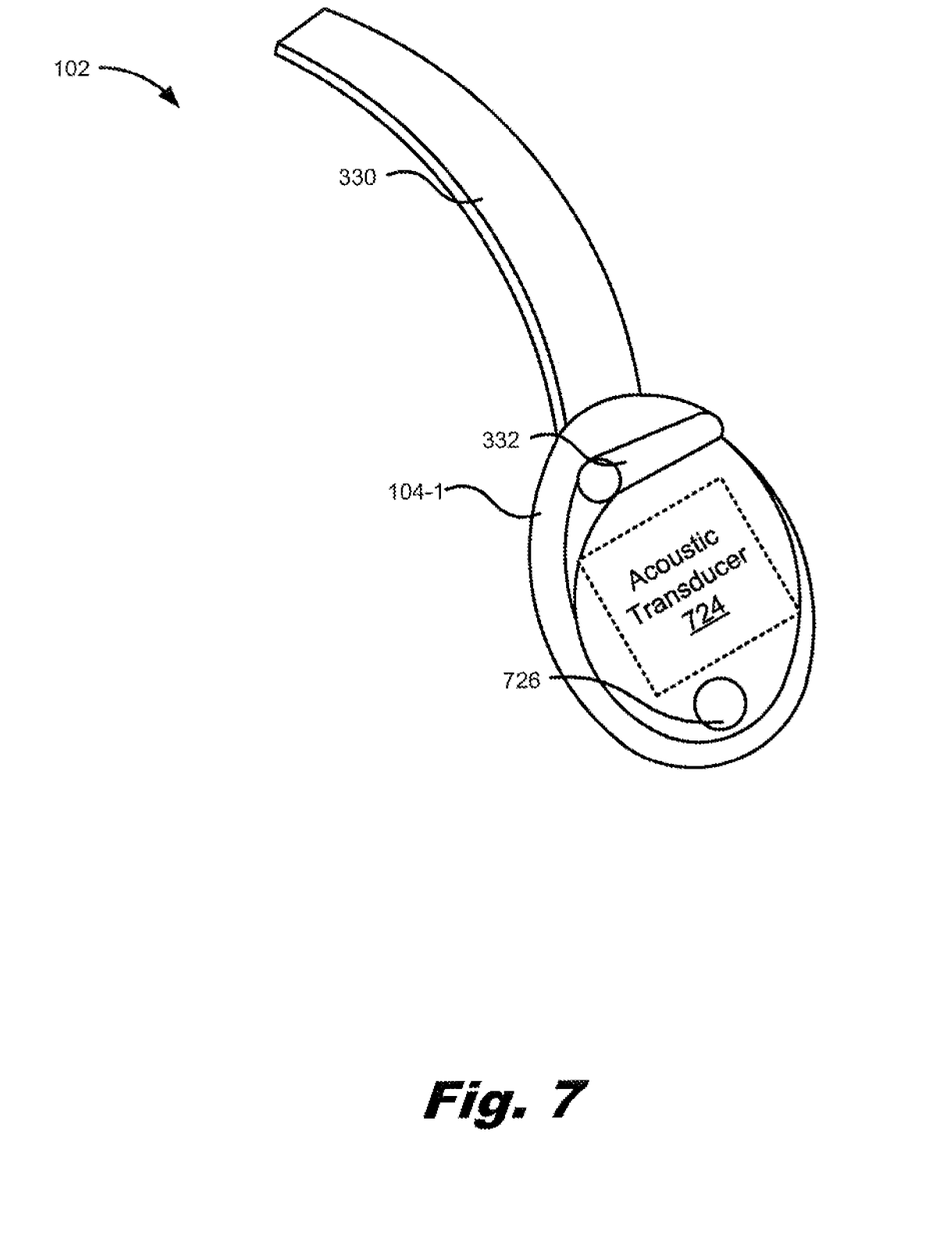
FIG. 7 is a diagram of a set of headphones with an acoustic transducer as a cooling mechanism, according to one example of principles described herein.

As illustrated, the cooling mechanism (110) in each of the cups is a semiconductor refrigeration chip (622) based on a Peltier effect, the processor (108) activates a refrigeration state of the semiconductor refrigeration chip (622) to regulate the environmental conditions inside of the cups (104) of the headphones (102) until the data for each of the sensors (106) indicates the environmental conditions match the environmental thresholds. In other examples, the headphones might include a single Peltier refrigeration chip with a fan to deliver cool air from the single chip to both speaker cups, FIG. 7 is a diagram of a set of headphones with an acoustic transducer as a cooling mechanism, according to one example of principles described herein. As will be described below, the cooling mechanism (110) is an acoustic transducer (724).

As illustrated, the cooling mechanism (110) in each of the cups is an acoustic transducer (724), the processor (108) activates the acoustic transducer (724) such that the acoustic transducer (724) exchanges air located inside of the cups (104) of the headphones (102) with air located external to the cups (104) via an aperture (726) or a number of apertures in each of the cups (104) until the data for each of the sensors (106) indicates the environmental conditions match the environmental thresholds. In an example, the speaker transducer in each cup may be used as an air pump, with an air intake aperture and an air outlet aperture provided in each cup. In another example, the apertures may have valves that may be actuated by the motion (e.g., pressure) of the transducer.

Figure 8:
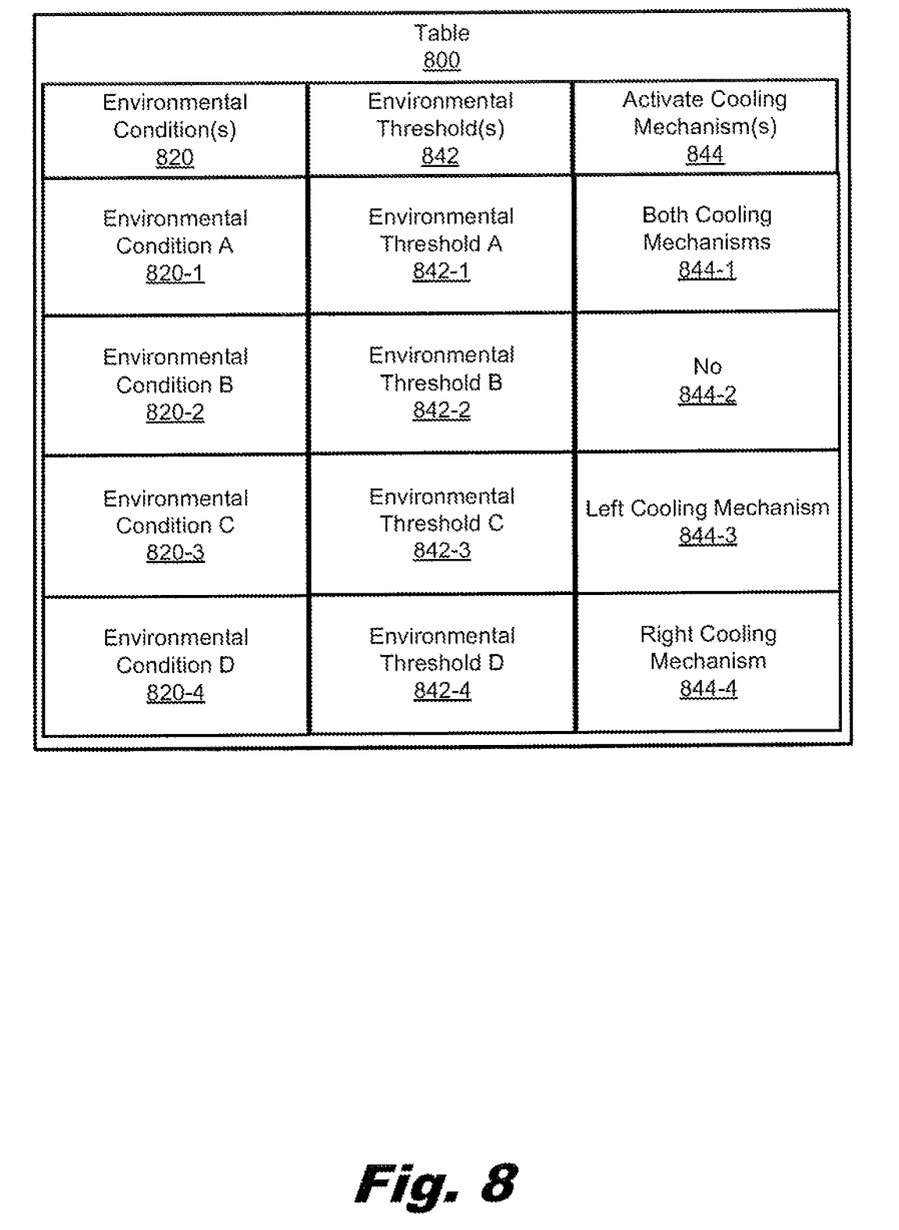
FIG. 8 is a diagram of a table with a number of thresholds, according to one example of principles described herein.

FIG. 8 is a diagram of a table used to explain various possible operating conditions of the headphones described herein. Each line of the table (800) includes environmental conditions (820), corresponding environmental thresholds (842) and a corresponding action with regard to activating the cooling mechanism(s) of the headphones. Each set of environmental conditions (820) includes an existing temperature, humidity level and heartrate of the user as described above. The corresponding environmental thresholds (842) including a threshold for each of these parameters that is set by the user or provided by the virtual reality device (112).

In the first example, environmental condition A (820-1), the sensors (106) indicate the temperature inside both of the cups (104) is 95 degrees, the humidity level is 40 percent and the user's heartrate is 80 beats per minute. In this example, environmental threshold A (842-1) indicates the temperature inside both of the cups (104) should be no more than 85 degrees, the humidity level no more than 30 percent and the user's heartrate no more than 70 beats per minute. Since all three types of sensors (106) indicate environmental threshold A (842-1) is exceeded, the cooling mechanism (110) in both cups (104) is activated (both 844-1).

In environmental condition B (820-2), the sensors (106) indicate the temperature inside both of the cups (104) is 85 degrees, the humidity level is 40 percent and the user's heartrate is 90 beats per minute. In this example, environmental threshold B (842-2) indicates the temperature inside both of the cups (104) should be no more than 90 degrees, the humidity level no more than 50 percent and the user's heartrate no more than 100 beats per minute. Since all three types of sensors (106) do not indicate environmental threshold B (842-1) is exceeded, the cooling mechanisms (110) in either of the cups (104) are not activated (no 844-2).

Environmental condition C (820-3), as indicated by the sensors (106), includes the temperature inside the left cup (104) at 95 degrees and 70 degrees in the right cup. The humidity level in both cups is 40 percent and the user's heartrate is 90 beats per minute. In this example, environmental threshold C (842-3) indicates the temperature inside both of the cups (104) should be no more than 90 degrees, the humidity level no more than 20 percent and the user's heartrate no more than 70 beats per minute. Since all three types of sensors (106) indicate environmental threshold C (842-3) is exceeded for the left cup, the cooling mechanism (110) in only the left cup (104) are activated (left 844-3).

Environmental condition D (820-4), as indicated by the sensors (106), includes the temperature inside the left cup (104) is 70 degrees and 92 degrees in the right cup. The humidity level in both cups is 40 percent and the user's heartrate is 90 beats per minute. In this example, environmental threshold D (842-4) indicates the temperature inside both of the cups (104) should be no more than 90 degrees, the humidity level no more than 20 percent and the user's heartrate no more than 70 beats per minute. Since all three types of sensors (106) indicate environmental threshold D (842-4) is exceeded for the right cup, the cooling mechanism (110) in only the right cup (104) is activated (right 844-4).

Figure 9:
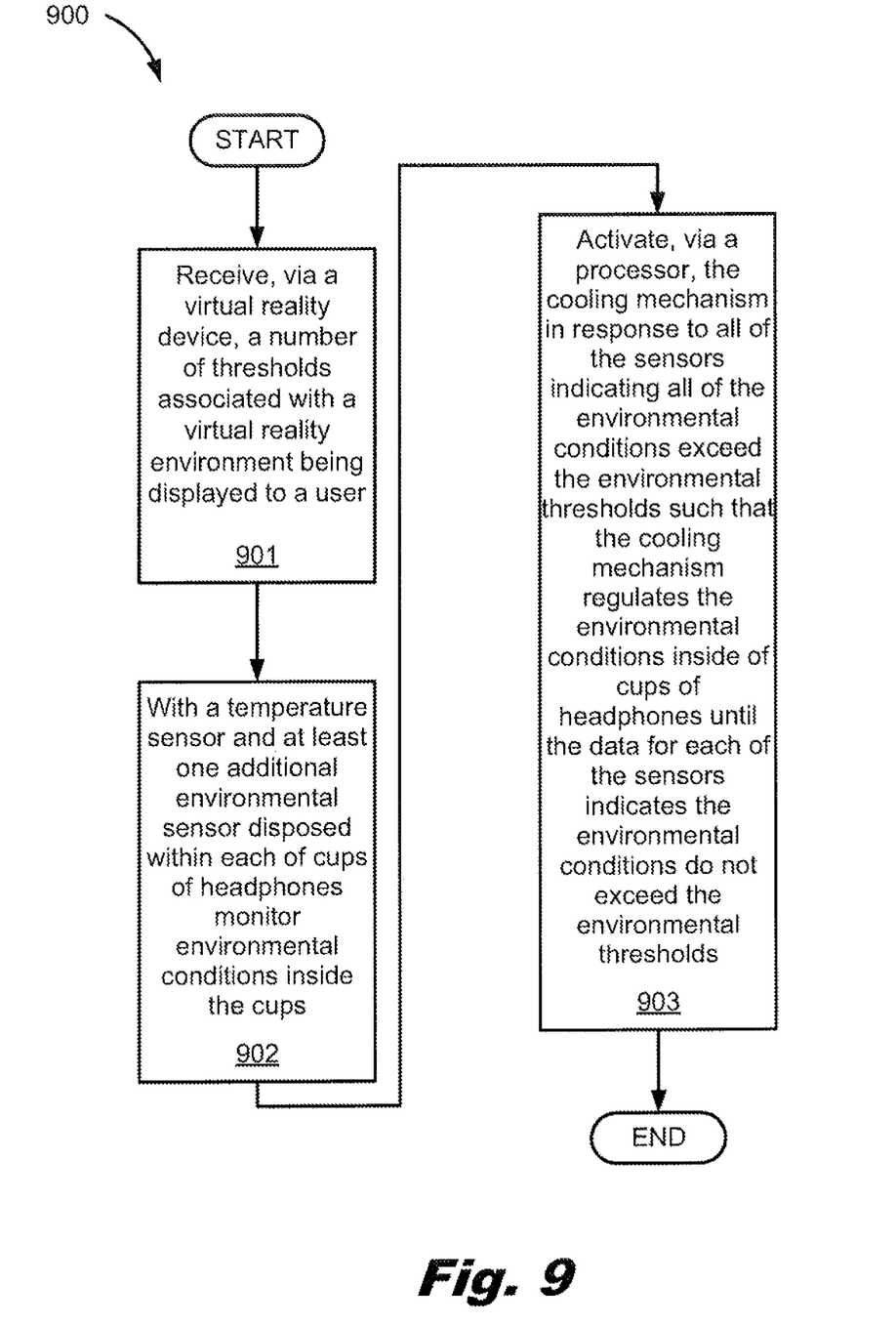
FIG. 9 is a flowchart of a method for regulating environmental conditions inside cups of a headset, according to one example of principles described herein.

FIG. 9 is a flowchart of a method for regulating environmental conditions inside cups of a headset, according to one example of principles described herein. In one example, the method (900) may be executed by the systems of FIGS. 1A to 7. In this example, the method (900) includes receiving (901), via a virtual reality device, a number of thresholds associated with a virtual reality environment being displayed to a user, with a temperature sensor and at least one additional environmental sensor disposed within each of cups of headphones, monitoring (902) environmental conditions inside the cups and activating (903), via a processor, the cooling mechanism in response to all of the sensors indicating all of the environmental conditions exceed the environmental thresholds such that the cooling mechanism regulates the environmental conditions inside of cups of headphones until the data for each of the sensors indicates the environmental conditions do not exceed the environmental thresholds.

As mentioned above, the method (900) includes receiving (901), via a virtual reality device, a number of thresholds associated with a virtual reality environment being displayed to a user. In an example, the thresholds associated with a virtual reality include a temperature threshold, a humidity threshold and a heartrate threshold.

As mentioned above, the method (900) includes a temperature sensor and at least one additional environmental sensor disposed within each of cups of headphones monitoring (902) environmental conditions inside the cups. In an example, the sensors include a temperature sensor, a humidity sensor, a heartrate sensor, or combinations thereof.

As mentioned above, the method (900) includes activating (903), via a processor, the cooling mechanism in response to all of the sensors indicating all of the environmental conditions exceed the environmental thresholds such that the cooling mechanism regulates the environmental conditions inside of cups of headphones until the data for each of the sensors indicates the environmental conditions do not exceed the environmental thresholds. In an example, if at least one of the sensors indicating at least one of the environmental conditions exceed one of the environmental thresholds, the method (900) activates the cooling mechanism such that the cooling mechanism regulates the environmental conditions inside the cups of headphones until the data for that the sensor indicates that environmental condition no longer exceeds that environmental threshold.

The preceding description has been presented to illustrate and describe examples of the principles described. This description is not intended to be exhaustive or to limit these principles to any precise form disclosed. Many modifications and variations are possible in light of the above teaching.

What is claimed is:

1. A set of headphones comprising:
    a pair of cups, each housing a speaker to be positioned over an ear of a user;
    a processor;
    a cooling mechanism disposed within each of the cups to regulate environmental conditions inside of the cups to match environmental thresholds provided by a virtual reality device displaying a virtual reality environment to the user; and
    a temperature sensor and at least one additional environmental sensor disposed within each of the cups to monitor the environmental conditions inside the cups;
    the processor to subsequently analyze data associated with the sensors and compare the data to the environmental thresholds; and
    the processor to, in response to the data for all of the sensors indicating all of the environmental conditions exceed all the environmental thresholds, activate the cooling mechanism such that the cooling mechanism regulates the environmental conditions inside of cups of headphones until the data for each of the sensors indicates the environmental conditions match the environmental thresholds.

2. The headphones of claim 1, wherein the at least one additional environmental sensor comprises a humidity sensor, a heartrate sensor or combinations thereof.

3. The headphones of claim 1, wherein the at least one additional environmental sensor comprises a humidity sensor, the humidity sensor to monitor a humidity level inside of the cups of the headphones such that when the humidity level inside of the cups of headphones exceeds a humidity threshold as indicated by one of the environmental thresholds, the cooling mechanism is activated to regulate the humidity level inside of the cups of the headphones until the humidity level inside of the matches the humidity threshold.

4. The headphones of claim 1, wherein the at least one additional environmental sensor comprises a heartrate sensor, the heartrate sensor to monitor a heartrate of the user wearing the headphones such that when the user's heartrate exceeds a heartrate threshold as indicated by one of the environmental thresholds, the cooling mechanism is activated to regulate the environmental conditions inside of the cups of the headphones to reduce the user's heartrate.

5. The headphones of claim 1, wherein the cooling mechanism in each of the cups comprises a motor rotatable coupled to a fan, the motor rotating the fan as instructed by the processor at a specified revolutions per minute (RPM) such that the fan exchanges air located inside of the cups of the headphones with air located external to the cups via an aperture in each of the cups until the data for each of the sensors indicates the environmental conditions match the environmental thresholds.

6. The headphones of claim 1, wherein the cooling mechanism in each of the cups comprises a semiconductor refrigeration chip based on a Peltier effect, the processor activating a refrigeration state of the semiconductor refrigeration chip to regulate the environmental conditions inside of the cups of the headphones until the data for each of the sensors indicates the environmental conditions match the environmental thresholds.

7. The headphones of claim 1, wherein the cooling mechanism in each of the cups comprises an acoustic transducer, the processor activating the acoustic transducer such that the acoustic transducer exchanges air located inside of the cups of the headphones with air located external to the cups via an aperture in each of the cups until the data for each of the sensors indicates the environmental conditions match the environmental thresholds.

8. The headphones of claim 1, wherein the cooling mechanism in each of the cups comprises a member and a actuator, the member is pivotally connected to the cup via a hinge such that, when the processor selectively activates the cooling mechanism, the actuator pivots the member to open an aperture through the cup such that air located inside of the cup of the headphones is exchanged with air located external to the cups until the data for each of the sensors indicates the environmental conditions match the environmental thresholds.

9. The headphones of claim 1, wherein the cooling mechanism in each of the cups comprises a member and a actuator, wherein the member is rotatably connected to the cup such that, when the processor selectively activates the cooling mechanism, the actuator rotates the member relative to the cup to open an aperture through the cup such that that air located inside of the cup of the headphones is exchanged with air located external to the cups until the data for each of the sensors indicates the environmental conditions match the environmental thresholds.

10. The headphones of claim 1, the processor to, based on the environmental conditions and thresholds, selectively activate the cooling mechanism in one of the two cups and not in the other cup.

11. The headphones of claim 1, wherein the processor is to use the environmental thresholds so that the environmental conditions inside the cups correspond to the virtual reality environment being displayed by the virtual reality device to the user.

12. The headphones of claim 1, wherein the processor is to download a file that tags a scene in the virtual reality environment being displayed to the user, the file comprising the environmental thresholds corresponding to the scene.

13. The headphones of claim 1, wherein the processor is to recognize one of the environmental thresholds as dominant and match the environmental conditions to the environmental thresholds based on one of the environmental thresholds being dominant over others.

14. A system comprising:
   a virtual reality device comprising an output to a virtual reality (VR) headset with headphones, the virtual reality device to provide the headset with environmental thresholds associated with a virtual reality environment being displayed to the user via the virtual reality device; and
   the VR headset with headphones further comprising:
     a pair of cups, each housing a speaker to be positioned over an ear of a user;
     a processor;
     a cooling mechanism disposed within each of the cups to regulate environmental conditions inside of the cups to match the environmental thresholds; and
     a temperature sensor and at least one additional environmental sensor disposed within each of the cups to monitor the environmental conditions inside the cups;
   the processor to subsequently analyze data associated with the sensors and compare the data to the environmental thresholds; and
   the processor to, in response to all of the sensors indicating all of the environmental conditions exceed the environmental thresholds, activate the cooling mechanism such that the cooling mechanism regulates the environmental conditions inside of cups of headphones until the data for each of the sensors indicates the environmental conditions do not exceed the environmental thresholds.

15. The system of claim 14, wherein the environmental thresholds are determined by a user when the headphones are not in communication with the virtual reality device.

16. The system of claim 14, wherein the cooling mechanism in each of the cups comprises a member and a actuator, the member is pivotally connected to the cup via a hinge such that, when the processor selectively activates the cooling mechanism, the actuator pivots the member to open an aperture through the cup such that air located inside of the cup of the headphones is exchanged with air located external to the cups until the data for each of the sensors indicates the environmental conditions match the environmental thresholds.

17. A method comprising:
   receiving, via a virtual reality device, a number of environmental thresholds associated with a virtual reality environment being displayed to a user;
   with a temperature sensor and at least one additional environmental sensor disposed within each of cups of headphones, monitoring environmental conditions inside the cups; and
   activating, via a processor, the cooling mechanism in response to all of the sensors indicating all of the environmental conditions exceed the environmental thresholds such that the cooling mechanism regulates the environmental conditions inside of cups of headphones until the data for each of the sensors indicates the environmental conditions do not exceed the environmental thresholds.

18. The method of claim 17, wherein the at least one additional environmental sensor comprises a humidity sensor.

19. The method of claim 17, wherein the at least one additional environmental sensor comprises a heartrate sensor.

20. The method of claim 17, further comprising:
   recognizing, with the processor, that one of the environmental thresholds is dominant; and
   matching the environmental conditions to the environmental thresholds based on one of the environmental thresholds being dominant over others.

* * * * *